United States Patent
Qian

(10) Patent No.: US 7,351,753 B2
(45) Date of Patent: *Apr. 1, 2008

(54) TWO-PART SELF-ADHERING DENTAL COMPOSITIONS

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/612,039

(22) Filed: Dec. 18, 2006

(65) Prior Publication Data

US 2007/0088097 A1    Apr. 19, 2007

Related U.S. Application Data

(63) Continuation of application No. 10/440,804, filed on May 19, 2003, now Pat. No. 7,166,651.

(51) Int. Cl.
*A61K 6/083*    (2006.01)

(52) U.S. Cl. .................. 523/115; 523/116; 523/117; 523/118

(58) Field of Classification Search ......... 523/115–118
See application file for complete search history.

(56) References Cited

U.S. PATENT DOCUMENTS

| | | | |
|---|---|---|---|
| 3,970,505 A | 7/1976 | Hauser et al. | |
| 3,991,008 A | 11/1976 | Temin et al. | |
| 4,569,976 A | 2/1986 | Zimmerman et al. | |
| 4,872,936 A | 10/1989 | Engelbrecht | |
| 5,063,257 A | 11/1991 | Akahane et al. | |
| 5,154,762 A | 10/1992 | Mitra et al. | |
| 5,639,808 A | 6/1997 | Coggio et al. | |
| 6,214,101 B1 | 4/2001 | Nakaseko | |
| 6,844,080 B2 | 1/2005 | Kneafsey et al. | |
| 7,166,651 B2 * | 1/2007 | Qian | 523/115 |
| 7,214,726 B2 * | 5/2007 | Qian | 523/116 |
| 2003/0134933 A1 | 7/2003 | Jin et al. | |
| 2005/0014861 A1 | 1/2005 | Qian | |

FOREIGN PATENT DOCUMENTS

| | | |
|---|---|---|
| EP | 0923924 B1 | 6/1999 |
| EP | 0948956 A2 | 10/1999 |
| WO | WO92/21314 | 12/1992 |
| WO | WO02/092023 A1 | 11/2002 |

OTHER PUBLICATIONS

3M ESPE, "RELYX Unicem Self-Adhesive Universal Resin Cement", Technical Product Profile, dated 2002, pp. 1-40.
European Search Report from EP04252780, dated Aug. 24, 2004.

* cited by examiner

*Primary Examiner*—Peter Szekely
(74) *Attorney, Agent, or Firm*—Wood, Herron & Evans, LLP

(57) ABSTRACT

A method of using a shelf-stable two-part self-adhering dental composition that comprises
(a) at least one acidic compound containing at least one acidic moiety selected from the group consisting of

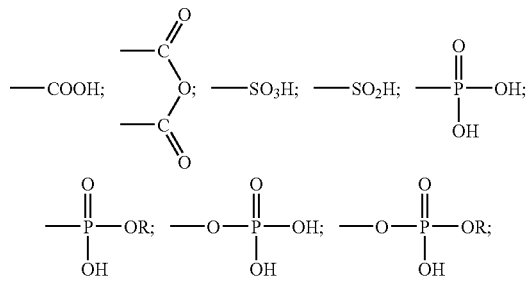

where R is an alkyl or aryl group;
(b) at least one polymerizable monomer without any acidic group where the polymerizable group is selected from the group consisting of an acrylate, a methacrylate and a vinyl group;
(c) a substituted thiourea selected from the group consisting of 1-(2-pyridyl)-2-thiourea and 1-(2-tetrahydrofurfuryl)-2-thiourea; and
(d) a hydroperoxide compound with at least one hydroperoxide group attached to a tertiary carbon. The first and second parts are then mixed immediately prior to application, applied to a dental substrate, and hardened. The bond strength of the mixed composition to dentine substrate is at least 3 MPa. The composition has excellent shelf-life and is self-adhering to various dental substrates such as a tooth, metal alloy and porcelain. It can be used as a filling material, a cement, a liner/base, a pit/fissure sealant, a primer or an adhesive.

11 Claims, No Drawings

TWO-PART SELF-ADHERING DENTAL COMPOSITIONS

RELATED APPLICATION

This application is a Continuation of U.S. patent application Ser. No. 10/440,804, now allowed, filed May 19, 2003, now U.S. Pat. No. 7,166,651 the disclosure of which is hereby incorporated herein by reference in its entirety.

FIELD OF THE INVENTION

The invention relates generally to a method of using a shelf-stable two-part self-adhering dental composition effective in initiating free radical polymerization in acidic environments and with an excellent shelf-life.

BACKGROUND OF THE INVENTION

The traditional procedure for bonding an indirect restoration, such as an inlay, onlay, or crown to a tooth structure is rather cumbersome. First the carious dentition is removed. The tooth is etched with an acidic etchant to remove the smear layer on the tooth surface, and the tooth is then coated with a thin layer of an acidic primer. The base and catalyst of a cement is mixed and applied to the bonding surface of the indirect restoration, and the restoration is then seated onto the primed tooth surface.

Cement hardening may be effected by self-curing by incorporating a self-cure initiator system, or by the combination of self-curing and photo-curing by using a photo-initiator. When metal is involved in the restorative material, such as a porcelain fused to a metal (PFM) crown, an efficient self-curing cement is needed because it is difficult for light to penetrate the restorative material and reach the cement with sufficient intensity to achieve adequate photo-curing.

The bonding procedure may be simplified by using a self-etching primer, eliminating the etch step, and thus accomplishing etching and priming in one step. The bonding procedure is simplified into the steps of applying a self-etching primer to the tooth and then applying a cement to the restoration material.

To further simplify the bonding procedure, it would be highly desirable to combine the steps of etching, priming, and cementing into one step. This would significantly shorten the chair time for certain restorative procedures. This would also significantly reduce the possibility for errors involved in the restorative procedure because only one step cementation would be involved.

Great difficulties, however, are encountered when combining the ingredients necessary to fulfill the functions of etching, priming, and cementing. For example, acidic compounds are used as an etchant or an etching primer, but the self-cure initiator commonly used in a resin cement is not effective under strongly acidic environments. The self-cure initiator system currently used by most manufacturers to effect self-curing of a resin cement comprises benzoyl peroxide and an aromatic tertiary amine. Two problems arise with use of this system. First, the aromatic tertiary amine loses its effectiveness immediately upon contact with a moderate or strong acid. Second, benzoyl peroxide is not very stable in acidic environments, quickly loses its potency and, therefore, has a rather short shelf-life. As a result, when a self-etching primer is incorporated into a resin cement, the mixed cement fails to harden because the redox initiators lose their potency under acidic environments. A simplified system which reduces or eliminates these difficulties is needed.

SUMMARY OF THE INVENTION

The invention is a self-adhesive, shelf-stable, two-part dental composition containing the following components:

(a) at least one acidic compound containing at least one acidic moiety selected from the group consisting of

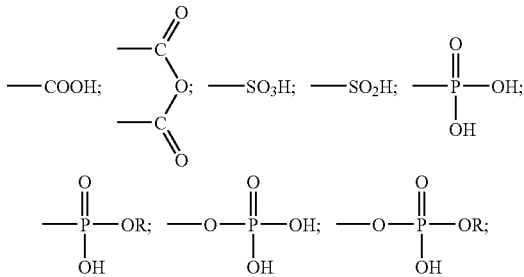

where R is an alkyl or aryl group;

(b) at least one polymerizable monomer without any acidic group where the polymerizable polymerizable group is selected from the group consisting of an acrylate, a methacrylate and a vinyl group;

(c) a substituted thiourea selected from the group consisting of 1-(2-pyridyl)-2-thiourea and 1-(2-tetrahydrofurfuryl)-2-thiourea; and (c) a hydroperoxide compound with at least one hydroperoxide group attached to a tertiary carbon.

The combination of a substituted thiourea activator, 1-(2-pyridyl)-2-thiourea and/or 1-(2-tetrahydrofurfuryl)-2-thiourea, and a hydroperoxide catalyst with the hydroperoxide group attached to a tertiary carbon, generates free radicals and initiates polymerization leading to hardening of the composition when the two parts containing the above activator and catalyst are mixed (it is a self-cure initiator system for hardening of the composition). The bond strength of the composition to a dentine substrate is at least 3 MPa.

An acidic self-adhering two-part dental composition incorporating this self-cure initiator system not only sets very well initially, but also continues to set effectively after both parts have been stored for an extended period of time. This results in simplified restorative procedures and significant time savings when the composition is used to bond to dental substrates such as dentine, enamel, dental alloys and porcelain, because etching and/or priming of the substrate is unnecessary. This self-adhering dental composition can be used as a dental restorative composition such as a dental filling material, cement, liner/base, pit/fissure sealant, primer or adhesive. The composition can also be used as an orthodontic composition or an endodontic composition. The composition may also contain one or more finely divided filler(s), a photo-initiator, a stabilizer, and/or a solvent.

One part of the composition contains the substituted thiourea and the other part of the composition contains the hydroperoxide compound. If the thiourea is encapsulated, using encapsulation methods known to one skilled in the art, for example water soluble or water insoluble encapsulants depending upon the particular components, the same part may contain both the encapsulated thiourea and the hydroperoxide compound. The two parts of composition may both be a paste (a paste/paste two-part composition), or may both be a liquid (a liquid/liquid two-part composition), or one part may be a powder and the other part may be a liquid (a powder/liquid two-part composition).

The invention also encompasses a method for providing the inventive dental composition to a patient. A two part composition is prepared comprising (a) at least one acidic compound containing at least one acidic moiety selected from the group consisting of

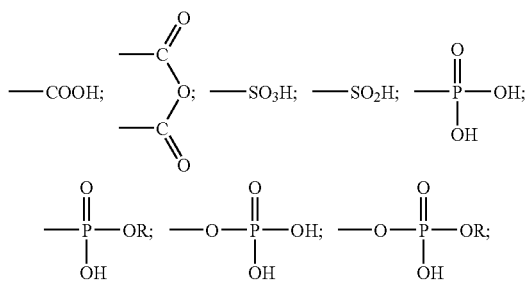

where R is an alkyl or aryl group;

(b) at least one polymerizable monomer without any acidic group where the polymerizable group is selected from the group consisting of an acrylate, a methacrylate and a vinyl group;

(c) a substituted thiourea selected from the group consisting of 1-(2-pyridyl)-2-thiourea and 1-(2-tetrahydrofurfuryl)-2-thiourea; and (d) a hydroperoxide compound with at least one hydroperoxide group attached to a tertiary carbon. The two parts are mixed immediately prior to application, and the mixed composition is then applied to a dental substrate. It is hardened by either self-curing, or combined self-curing and photo-curing.

In one embodiment the composition is a two-part paste/paste. The first paste contains at least one polymerizable monomer with a polymerizable group selected from the group consisting of an acrylate, a methacrylate and a vinyl group; a substituted thiourea selected from the group consisting of 1-(2-pyridyl)-2-thiourea and 1-(2-tetrahydrofurfuryl)-2-thiourea; and a finely divided filler. The second paste contains at least one acidic compound containing at least one acidic moiety selected from the group consisting of

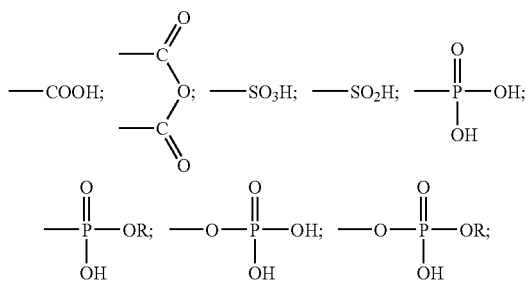

where R is an alkyl or aryl group; at least one polymerizable monomer without any acidic group with a polymerizable group selected from the group consisting of an acrylate, a methacrylate, and a vinyl group; and a hydroperoxide compound with at least one hydroperoxide group attached to a tertiary carbon; and a finely divided filler.

In another embodiment the composition is a two-part powder/liquid. The powder contains at least a substituted thiourea selected from the group consisting of 1-(2-pyridyl)-2-thiourea and 1-(2-tetrahydrofurfuryl)-2-thiourea; and a finely divided filler. The liquid contains at least one acidic compound containing at least one acidic moiety selected from the group consisting of

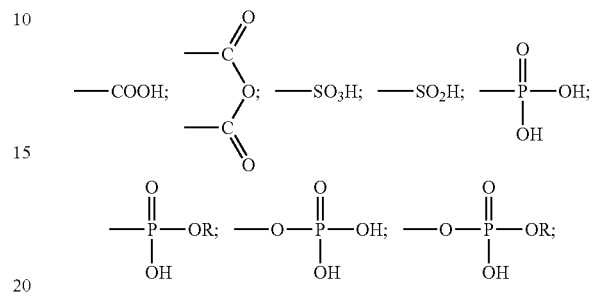

where R is an alkyl or aryl group; at least one polymerizable monomer/oligomer without any acidic group where the polymerizable group is selected from the group consisting of an acrylate, a methacrylate, and a vinyl group; and a hydroperoxide compound with at least one hydroperoxide group attached to a tertiary carbon.

These and other advantages will be apparent in light of the following detailed description and examples.

DETAILED DESCRIPTION OF THE INVENTION

A dental compositon which etches, primes, and cements in one step, and is shelf stable, is disclosed. The composition can be used as a restorative dental composition, an endodontic composition, and an orthodontic composition, and has the following components:

(a) at least one acidic compound containing at least one acidic moiety selected from the group consisting of

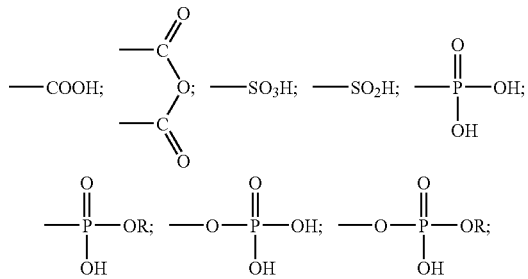

where R is an alkyl or aryl group;

(b) at least one polymerizable monomer without any acidic group where the polymerizable group is selected from the group consisting of an acrylate, a methacrylate, and a vinyl group;

(c) a substituted thiourea selected from the group consisting of 1-(2-pyridyl)-2-thiourea and 1-(2-tetrahydrofurfuryl)-2-thiourea; and (d) a hydroperoxide compound with at least one hydroperoxide group attached to a tertiary carbon.

The composition is two parts, with the base and catalyst mixed immediately prior to application, as known to one skilled in the art, so that it can set quickly. In various embodiments, the base and catalyst are mixed within about ten minutes prior to application, within about five minutes prior to application, or within about two minutes prior to application.

The combination of a substituted thiourea activator selected from the group consisting of 1-(2-pyridyl)-2-thiourea and 1-(2-tetrahydrofurfuryl)-2-thiourea, and a hydroperoxide catalyst with the hydroperoxide group attached to a tertiary carbon provides a self-cure initiator system for cement hardening. An acidic self-adhering two-part dental composition incorporating this self-cure initiator system not only sets very well initially, but also continues to set effectively even after each part is subjected to accelerated aging at elevated temperatures for several weeks (for example, five weeks at 37° C.). Much simplified restorative procedures and significant time savings result when the composition is used to bond to dental substrates such as dentine, enamel, dental alloys and porcelain, because etching and/or priming of the substrate is unnecessary. The self-adhering dental composition, incorporating the above self-cure initiator, can be used as a dental filling material, cement, liner/base, pit/fissure sealant, primer or adhesive, and etching and priming of the substrate is optional and can be omitted.

One or more additional components may be included in the inventive composition. The additional components include at least one finely divided filler, a photo-initiator, a solvent, and/or stabilizer, and may be incorporated into either part or both parts. In embodiments of the invention the acidic compound of the composition is polymerizable and contains at least one ethylenically unsaturated moiety selected from the group consisting an acrylate, a methacrylate, and a vinyl group.

The method for using the inventive composition includes mixing the two parts of the composition just prior to application, then applying the mixed composition to a dental substrate such as dentine, enamel, dental alloy, or porcelain, and hardening the composition by self-curing (without a photo-initiator) or by the combination of self-curing and photo-curing (with a photo-initiator). The resulting bond strength of the mixed composition to a dentine substrate is at least 3 MPa.

For component (a), any acidic compound with at least one acidic group selected from the group consisting of following can be used:

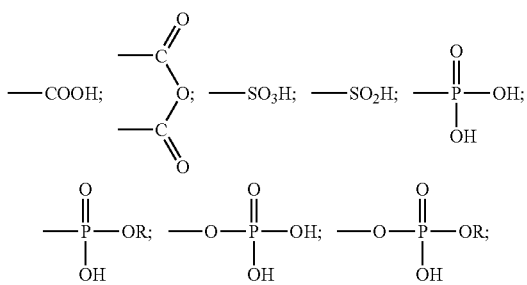

where R is an alkyl or aryl group.

Examples include, but are not limited to, maleic acid, itaconic acid, methacrylic acid, acrylic acid, tartaric acid, ethylenediaminetetraacetic acid (EDTA), EDTA salt, citric acid, homopolymer or copolymer of an α,β-unsaturated carboxylic acid such as poly(acrylic acid), copolymer of acylic acid such as poly(acylic acid-maleic acid) copolymer or poly(acrylic acid-itaconic acid) copolymer or poly(acrylic acid-maleic acid-itaconic acid) copolymer, polymerizable homopolymer or copolymer of an α,β-unsaturated carboxylic acid such as (meth)acrylated poly(acrylic acid) (where (meth)acrylated=acrylated or methacrylated), (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, trimellitic anhydride, 4-methacryloxyethyltrimellitic anhydride (4-META), any addition product of mono- or di-anhydride compound with a hydroxyalkylmethacrylate compound such as PM-HEMA (addition product of pyromellitic acid anhydride and 2-hydroxyethyl methacrylate), PM-GDM (addition product of pyromellitic acid anhydride and glycerol dimethacrylate), BTDA-HEMA (addition product of 3,3',4,4'-benzophenonetetracarboxylic dianhydride and hydroxyethyl methacrylate), and PA-HEMA (addition product of phthalic anhydride and hydroxyethyl methacrylate), MA-GDM (addition product of maleic anhydride and glycerol dimethacrylate), sulfuric acid, alkyl sulfonic acid, aromatic sulfonic acid, alkyl sulfinic acid, aromatic sulfinic acid, phosphoric acid, pyrophosphoric acid, monoalkyl phosphate, dialkyl phosphate, aryl alkyl phosphate, aryl phosphate, phenyl-P (phenyl methacryloxyethyl phosphate), glyceryldimethacrylate phosphate (GDM-P), pentaerithritol triacrylate phosphate (PENTA-P), methacryloyloxydecyl phosphate (MD P), hydroxyethyl methacrylate phosphate (HEMA-P), bis(hydroxyethylmethacrylate) phosphate (bis(HEMA)-P), and combinations thereof.

In specific embodiments, acidic compounds are those having at least one acidic group and at least one ethylenically unsaturated moiety selected from the group consisting of an acrylate, a methacrylate, and a vinyl group, so that it can copolymerize with other monomers. Examples of acidic compounds having at least one acidic group and at least one ethylenically unsaturated moiety include, but are not limited to, (meth)acrylated poly(acrylic acid), (meth)acrylated poly (acrylic acid) copolymer such as (meth)acrylated poly (acrylic acid-maleic acid) copolymer and (meth)acrylated poly(acrylic acid-maleic acid-itaconic acid) copolymer, 4-META, PM-GDM, PM-HEMA, BTDA-HEMA, PA-HEMA, MA-GDM, phenyl-P, GDM-P, PENTA-P, MDP, HEMP-P, and Bis(HEMA)-P. In other embodiments, acidic compounds are those having at least one phosphate group and at least one ethylenically unsaturated moiety selected from the group consisting of an acrylate, a methacrylate, and a vinyl group, so that it can copolymerize with other monomers. Examples of acidic compounds having at least one phosphate group and at least one ethylenically unsaturated moiety include, but are not limited to, phenyl-P, GDM-P, PENTA-P, MDP, HEMP-P, and Bis(HEMA)-P.

In one embodiment, the concentration of the total acidic compound or compounds is at least 10% (w/w) in the overall composition (excluding filler and solvent). In another embodiment, the concentration of the total acidic compound or compounds is at least 15% (w/w) in the overall composition (excluding filler and solvent). In another embodiment, the concentration of the total acidic compound or compounds is at least 20% (w/w) in the overall composition (excluding filler and solvent).

For component (b), at least one polymerizable monomer without any acidic group can be used. A polymerizable monomer includes any monomer having at least one ethylenically unsaturated moiety selected from the group consisting of an acrylate, a methacrylate, and a vinyl group. In specific embodiments, the ethylenically unsaturated group is selected from acrylate and methacrylate groups. Examples of polymerizable monomers include, but are not limited to, the following: hydroxyethyl (meth)acrylate {(meth) acrylate=acrylate or methacrylate}, hydroxypropyl (meth) acrylate, hydroxybutyl (meth)acrylate; glycerol di(meth) acrylate, glycerol mono(meth)acrylate, methyl (meth) acrylate, ethyl (meth)acrylate, propyl (meth)acrylate, butyl (meth)acrylate, hexyl (meth)acrylate, octyl (meth)acrylate, lauryl (meth)acrylate, decyl (meth)acrylate, tridecyl (meth) acrylate; 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth) acrylate (TEGDMA), tetraethyleneglycol di(meth)acrylate, polyethyleneglycol mono-(meth)acrylate, polyethyleneglycol di-(meth)acrylate, polypropyleneglycol mono-(meth) acrylate, polypropyleneglycol di-(meth)acrylate, polytetramethyleneglycol mono-(meth)acrylate, polytetramethyleneglycol di-(meth)acrylate, hexanediol di(meth)acrylate, trimethyloylpropane tri(meth)acrylate, UDMA (reaction product of 2-hydroxyethyl methacrylate with 2,4,4 -trimethylhexane diisocyanate), 2,2-bis[4-(2-hydroxy-3-methacryloylpropoxy)-phenyl]-propane (BisGMA), ethoxylated bisphenol A dimethacrylate (EB-PADMA-n where n=total number of moles of ethylene oxide in the molecule, as only one example n=2-20 units) in tetrahydrofurfuryl (meth)acrylate, or mixtures thereof.

For component (c), a substituted thiourea selected from the group consisting of 1-(2-pyridyl)-2-thiourea and 1-(2-tetrahydrofurfuryl)-2-thiourea is used. In one embodiment, 1-(2-pyridyl)-2-thiourea is used. In one embodiment the concentration of total substituted thiourea(s) is in the range of about 0.01% (w/w) to about 10.0% (w/w) of the overall composition. In another embodiment, the concentration is in the range of about 0.1% (w/w) to about 3.0% (w/w) of the overall composition.

For component (d), any hydroperoxide compound with at least one hydroperoxide group attached to a tertiary carbon can be used. The hydroperoxide compound can contain more than one hydroperoxide group. Examples of hydroperoxide compounds include, but are not limited to, t-butyl hydroperoxide, t-amyl hydroperoxide, p-diisopropylbenzene hydroperoxide, cumene hydroperoxide, pinane hydroperoxide, p-methane hydroperoxide, and 1,1,3,3-tetramethylbutyl hydroperoxide. The concentration of total hydroperoxide compound(s) is in the range of about 0.01% (w/w) to about 10.0% (w/w) of the overall composition. In one embodiment, it is in the range of about 0.1% (w/w) to about 5.0% (w/w) of the overall composition. The above mentioned hydroperoxides are stable under acidic condition and have a long shelf-life.

The self-cure initiator, using the combination of the above described substituted thiourea and the hydroperoxide compound, is used in a two-part self-adhering self-cure dental composition (i.e. curing without the activation of the light), or a dual-cure dental composition (both self-curing and photo-curing) when a photo-initiator is also included. When the two-parts are mixed and self-cured without photo-curing, the mixed composition sets or hardens in less than about 30 minutes, and in some embodiments in less than about 20 minutes and in less than about 10 minutes, from the start of mixing. These setting times occur even after both parts of the composition have been subjected to aging for five weeks at 37° C., indicating the shelf-stability of the composition.

The substituted thiourea, unless it is microencapsulated, is incorporated into the part without any acidic compound. If the substituted thiourea is encapsulated, it may be incorporated into either part of the composition. Also, unless the substituted thiourea is microencapsulated, the substituted thiourea and hydroperoxide compound are incorporated into separate parts of the composition. If the substituted thiourea is microencapsulated, it may be incorporated into the same part of the composition that contains the hydroperoxide compound.

The composition also can include one or more of a finely divided filler, a photo-initiator, a stabilizer, and/or a solvent.

One or more fillers can be incorporated into the composition. The filler(s) enhance mechanical properties, reduce polymerization shrinkage, improve rheological properties, and increase radiopacity for easy detection of gaps or voids. Examples of fillers include, but are not limited to, inorganic metal, salt, oxide, nitride, silicate glass, aluminosilicate glass, luminoborosilicate glass, fluoroaluminosilicate glass, quartz, colloidal silica, precipitated silica, zirconia-silica, polymeric filler, polymerized composite filler with inorganic particles, and the combination thereof. Inorganic fillers for increased x-ray contrasting ability include metals, salts, oxides, silicate glass, aluminosilicate glass, aluminoborosilicate glass, and fluoroaluminosilicate glass containing elements of high atomic number such as Sr, Y., Zr, Ba, La, Hf, Zn, Bi, W, and rare earth metal, and a combination thereof. Examples include barium sulfate, silver, strontium fluoride, barium fluoride, ytterbium fluoride, yttrium fluoride, barium tungstate, zinc oxide, bismuth(III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, etc. Fumed silica, colloidal silica, or precipitated silica can also be incorporated to improve the dispersion of the filler as well as the rheological and handling properties of the material. Examples of colloidal silicas are Aerosil series such as OX-50, OX-130, and OX-200 silica sold by Degussa (Ridgefield Park, N.J.), and Cab-O-Sil M5 and Cab-O-Sil TS-530 silica sold by Cabot Corp (Tuscola, Ill). The filler also includes nanoparticles such as those obtained through a sol-gel process. Examples include those disclosed in U.S. Pat. Nos. 4,567,030 and 5,609,675, the disclosure of each is expressly incorporated by reference herein in its entirety. Mixtures of different fillers can be used.

For inorganic fillers, the surface of the filler may be treated or coated with a coupling agent such as γ-methacryloyloxypropyltrimethoxysilane (MPTMS). This enhances the interfacial bonding between the filler and resin matrix, and improves mechanical properties. In various embodiments, the mean particle size of the filler is less than 50 microns, and the mean particle size may be less than 10 microns. The concentration range of total filler(s) is in the range of 0% to about 95% by weight. The concentration range depends on the application. For primer or adhesive applications, the specific concentration of filler(s) may be in the range of 0% to about 65% by weight. For cement applications, the concentration of filler(s) may be in the range of about 20% to about 75% by weight. For filling materials, the concentration of filler(s) may be in the range of about 40% to about 90% by weight.

A photo-initiator can be used to make the composition dual-curable, i.e., both self-curable (in the absence of light) and photo-curable. Examples of photo-initiators include, but are not limited to, benzoin, benzoin ethers and esters, 2,2-diethoxy acetophenone, diketone compounds such as camphoroquinone and 1 -phenyl-1,2-propanedione, monoacylphosphine oxide, bisacylphosphine oxide as described in U.S. Pat. No. 4,792,632, which is expressly incorporated by reference herein in its entirety, diaryliodonium salt, triarylsulfonium salt, and a mixture of photo-initiators. Additionally, an activator can be used together with photo-initiators to enhance the curing efficiency. Activators include, but are not limited to, tertiary amines and sulfinate compounds. Examples of activators include, but are not limited to, ethyl 4-(N,N-dimethylamino)benzoate, 2-(ethylhexyl)-4-(N,N-dimethylamino)benzoate, N,N-dimethylaminoethyl methacrylate, N,N-dimethylaminophenethyl alcohol, sodium benzenesulfinate, and sodium toluenesulfinate. In embodiments, photo-initiator systems include the combination of camphoroquinone and a tertiary amine such as ethyl 4-(N, N-dimethylamino)benzoate, 2-(ethylhexyl)-4-(N,N-dimethylamino) benzoate, N,N-dimethylaminoethyl methacrylate, N,N-dimethylaminophenethyl alcohol. The components of the photo-initiator system can be incorporated into either part or both parts of the composition.

A solvent can also be incorporated into the inventive composition. Useful solvents include water, methanol, ethanol, isopropanol, acetone, ethylene glycol, glycerin, and methyl ethyl ketone (MEK).

Other ingredients can also be incorporated into the inventive composition, such as colorants, stabilizers, UV absorbers, and antimicrobial additives. Colorants are used to achieve desired shades and can be inorganic pigments or organic dyes. The stabilizer is a polymerization inhibitor to improve the shelf stability of the restorative material. Most commonly used stabilizers include 2,6-di-(tert-butyl)-4-methylphenol (BHT) and 4-methoxyphenol (MEHQ). UV absorbers improve the color stability of the restorative material upon exposure to UV light. An example of a UV absorber is 2-hydroxy-4-methoxybenzophenone (UV-9).

The inventive composition can be a powder/liquid configuration (one part is in powder form and the other is in liquid form), a liquid/liquid configuration (both parts are in liquid form), and paste/paste configuration (both parts are in paste form).

An example of a paste/paste two-part self-adhering dental composition is a first paste comprising one or more polymerizable monomer, a substituted thiourea such as 1-(2-pyridyl)-2-thiourea, and one or more finely divided fillers; and a second paste comprising an acidic compound, a hydroperoxide, one or more non-acidic polymerizable monomer, and one or more finely divided fillers as a minimum. A photo-initiator can also be incorporated. In some embodiments the acidic compound is a polymerizable monomer. The two parts are mixed just prior to application, applied to a dental substrate, and hardened inside a patient's mouth by self-curing or the combination of self-curing or light-curing. A solvent may be optionally incorporated into either paste. If the substituted thiourea is microencapsulated, both the substituted thiourea and the hydroperoxide catalyst can be incorporated into either paste, and may be incorporated into the same paste.

An example of a powder/liquid two-part self-adhering dental composition is a first part of a powder blend comprising a substituted thiourea such as 1-(2-pyridyl)-2-thiourea, and one or more finely divided fillers; and a second part of a liquid mixture comprising an acidic compound, a hydroperoxide, one or more non-acidic polymerizable monomer. A photo-initiator can also be incorporated. In one embodiment, the acidic compound is a polymerizable monomer. The two parts are mixed just prior to application, applied to a dental substrate, and hardened inside a patient's mouth by self-curing or the combination of self-curing and light-curing. A solvent may be optionally incorporated into the liquid.

An example of a liquid/liquid two-part self-adhering dental composition is a first liquid mixture comprising one or more polymerizable monomers, a substituted thiourea such as 1-(2-pyridyl)-2-thiourea, and optionally a solvent such as ethanol; and the second liquid mixture comprises an acidic compound, a hydroperoxide, one or more non-acidic polymerizable monomers, and optionally a solvent such as acetone, ethanol, and/or water. A photo-initiator can also be incorporated. The acidic compound in one embodiment is a polymerizable monomer and/or a polymerizable polymer such as (meth)acrylated homopolymer or copolymer of an $\alpha,\beta$-unsaturated carboxylic acid. The two are mixed just prior to application, applied to a dental substrate, and hardened inside a patient's mouth by self-curing or the combination of self-curing and light-curing.

The inventive composition is used in formulating restorative materials, such as a filling material, a cement, a base/liner, a pit/fissure sealant, a primer, or an adhesive. The inventive composition is also used in formulating orthodontic materials, such as an orthodontic primer, adhesive, and cement. The inventive composition is also used in formulating endodontic materials such as an endodontic primer, adhesive, cement, sealing or filling material.

The invention also includes a method for first preparing the shelf-stable two-part self-adhering dental composition as described, mixing the two parts prior to application, applying the mixed composition to a dental substrate such as dentine, enamel, dental metal alloy and porcelain, and hardening the mixture either by self-curing or the combination of self-curing and photo-curing. The bond strength of the mixed composition to a dentine substrate is at least 3 MPa in one embodiment, and is at least 5 MPa in another embodiment. Mixing of the two parts can be achieved by any mixing means, including hand mixing using a spatula, a mixing stick, or a brush; mixing by an automated mixing device such as an amalgamator, wherein the composition is contained in a capsule and the two parts are separated by a membrane or film; or by using a static mixer attached to the openings of a dual syringe assembly. Use of a static mixer attached to a dual syringe assembly may be used with a two-part paste/paste composition, with each syringe containing one paste.

The two parts can be mixed in any weight ratio as long as the mixed material can set within about thirty minutes after the mixed material is applied to the dental substrate.

The following examples illustrate how the current invention is applied and do not limit the scope of the invention.

EXAMPLES

Only two-part dual-cure self-adhering cement compositions were formulated and tested in the following examples. Other configurations such as self-cure vs. dual-cure;

filled vs. unfilled; cement vs. filling material, liner/base, primer or adhesive; composite resin vs. hybrid material such as compomer or resin-modified glass-ionomer can be easily obtained by incorporating different curing initiators (self-cure initiator or a combination of self-cure initiator and photo-initiator), filler type (reactive filler and/or non-reactive filler with acid), and viscosity (varying filler concentration, solvent).

The following abbreviations are used in all examples:

| | |
|---|---|
| ATU: | 1-acetyl-2-thiourea |
| Barium Glass: | bariumaluminoborosilicate filler that has an mean particle size of 1.0 micron and its surface was treated with MPTMS |
| BHT: | 2,6-di-(tert-butyl)-4-methylphenol |
| Bis-GMA: | 2,2-bis[4-(2-hydroxy-3-methacryloylpropoxy)-phenyl]-propane |
| BPO: | benzoyl peroxide |
| CHP: | cumene hydroperoxide |
| CQ: | camphoroquinone |
| DHEPT: | N,N-Dihydroxyethyl-p-toluidine |
| DMAPE: | 4-(dimethylamino)phenethyl alcohol. |
| EBPADMA-4: | ethoxylated bisphenol A dimethacrylate with 4 moles of ethylene oxide |
| EDMAB: | ethyl 4-(N,N-dimethylamino) benzoate |
| ETMPTA: | ethoxylated trimethylolpropane triacrylate with 3 moles of ethylene oxide |
| GDM: | glyceryldimethacrylate |
| GDM-P: | glyceryldimethacrylate phosphate |
| HEMA: | hydroxyethyl methacrylate |
| MEHQ: | 4-methoxyphenol |
| MHP: | p-methane hydroperoxide |
| MPTMS: | γ-methacryloyloxypropyltrimethoxysilane |
| PA-HEMA: | addition product of phthalic anhydride and hydroxyethylmethacrylate (HEMA) |
| PHP: | pinane hydroperoxide |
| PTU: | 1-(2-pyridyl)-2-thiourea |
| Sr/Zn FAS Glass: | strontiumzincfluoroaluminosilicate glass that has an mean particle size of 4.0 microns and its surface was treated with MPTMS |
| ST-OX-50: | fumed silica OX-50 surface treated with MPTMS |
| PEG-400 DMA: | polyethyleneglycol-400 dimethacrylate |
| TAHP: | t-amyl hydroperoxide |
| TEGDMA: | triethyleneglycol dimethacrylate |
| TMBHP: | 1,1,3,3-tetramethylbutyl hydroperoxide |
| TS-530: | surface treated fumed silica or colloidal silica sold by Cabot Corp. |
| UDMA: | reaction product of 2-hydroxyethyl methacrylate with 2,4,4-trimethylhexane diisocynate |

Example 1 (Comparative Example)

The following adhesive cement formulas comprising base paste (B-1) using DHEPT as an activator and catalyst pastes (C-1 & C-2) using benzoyl peroxide (BPO) as catalyst were made for comparison purposes. Acidic monomer GDM-P was incorporated in the catalyst paste C-2 while GDM-P was replaced with non-acidic monomer GDM in catalyst paste C-1. In making all the pastes in this and the following examples, first all the monomers and any ingredients soluble in the resin mixture were mixed together to make a homogeneous liquid mixture, and the then the fillers (TS-530, ST-OX-50, Sr/Zn FAS Glass, or Barium Glass) were blended into the liquid mixture to make the paste. For testing set time in all the examples, the base and catalyst pastes were mixed in 1:1 ratio (weight).

| | B-1 |
|---|---|
| BisGMA | 8.65 |
| UDMA | 7.22 |
| PEG-400 DMA | 4.33 |
| ETMPTA | 2.89 |
| HEMA | 5.77 |
| CQ | 0.09 |
| MEHQ | 0.014 |
| DMAPE | 0.13 |
| DHEPT | 0.41 |
| TS-530 | 3.00 |
| ST-OX-50 | 4.72 |
| Sr/Zn FAS Glass | 62.78 |

| | C-1 | C-2 |
|---|---|---|
| BisGMA | 6.56 | 6.56 |
| GDM | 16.40 | — |
| GDM-P | — | 16.40 |
| HEMA | 6.56 | 6.56 |
| ETMPTA | 3.27 | 3.27 |
| BHT | 0.05 | 0.05 |
| BPO | 0.66 | 0.66 |
| TS-530 | 2.00 | 2.00 |
| ST-OX-50 | 3.22 | 3.22 |
| Barium Glass | 61.28 | 61.28 |

The self-cure initiator system comprising DHEPT and BPO pair is currently used in most dental resin cement formulations that contains no strongly acidic compound or monomer. CQ and DMAPE constitute a photo-initiator system although DMAPE also functions as a co-activator for a self-cure initiator. When catalyst paste C-1 containing no acidic monomers was mixed with base paste B-1 for 30 seconds using a spatula, the mixed material hardened or set after 2 minutes 41 seconds (2'41"). However, when freshly prepared catalyst paste C-2 containing acidic monomer GDM-P was mixed with base paste B-1, the mixed material failed to harden within 30 minutes. This could be caused by the instability of BPO under acidic condition and also quick loss of efficacy of DHEPT upon exposure to acidic monomer GDM-P. Therefore, the acidic adhesive cement using traditional self-cure initiator had no shelf-life and would not set-up upon mixing of freshly prepared base and catalyst pastes.

Example 2

A catalyst paste (C-3) similar to C-2 in Example 1 was made by replacing BPO with cumene hydroperoxide (CHP) as the catalyst.

| | C-3 |
|---|---|
| BisGMA | 6.45 |
| GDM-P | 16.13 |
| HEMA | 6.45 |
| ETMPTA | 3.23 |
| BHT | 0.05 |
| CHP | 1.19 |
| TS-530 | 2.00 |
| ST-OX-50 | 3.22 |
| Barium Glass | 61.28 |

Two base pastes (B-2 and B-3) similar to B-1 in Example 1 were made by replacing DHEPT with 1-acetyl-2-thiourea (ATU) and 1-(2-pyridyl)-2-thiourea (PTU) respectively.

| | B-2 | B-3 |
|---|---|---|
| BisGMA | 8.65 | 8.65 |
| UDMA | 7.22 | 7.22 |
| PEG400DMA | 4.33 | 4.33 |
| ETMPTA | 2.89 | 2.89 |
| HEMA | 5.77 | 5.77 |

-continued

|  | B-2 | B-3 |
|---|---|---|
| CQ | 0.09 | 0.09 |
| MEHQ | 0.014 | 0.014 |
| DMAPE | 0.13 | 0.13 |
| ATU/PTU | 0.41 (ATU) | 0.41 (PTU) |
| TS-530 | 3.00 | 3.00 |
| ST-OX-50 | 4.72 | 4.72 |
| Sr/Zn FAS Glass | 62.78 | 62.78 |

The combination of B-2 and C-3 had an initial set time of 4'21" and the combination of B-3 and C-3 had an initial set time of 3'28". The catalyst paste C-3 was then subjected to accelerated aging at 37° C. and the set time was tested every week with respective bases (B-2 and B-3) that were stored at ambient temperature.

Set time tested against catalyst C-3 (stored at 37° C.)

|  | Base B-2 (ATU) | Base B-3 (PTU) |
|---|---|---|
| Initial | 4'21" | 3'28" |
| 1 week | 9'00" | 3'40" |
| 2 weeks | 11'42" | 4'50" |
| 3 weeks | 20'15" | 5'18" |
| 4 weeks | — | — |
| 5 weeks | >35'00" | 9'50" |

The combination of B-2 (ATU) and C-3 (CHP) had an initial set time of 4'21", significant improvement over the conventional DHEPT and BPO initiator system in Example 1. However, the setting reaction of the B-2 (ATU)/C-3 (CHP) pair slowed significantly after three weeks, and its set time increased to 20'15" and failed to set after 35 minutes after five weeks. The combination of B-3 (PTU)/C-3 (CHP) yielded a more stable system than B-2 (ATU)/C-3 (CHP) pair, and still set within 10 minutes after five weeks of aging.

Example 3

Two more catalyst pastes (C-4 and C-5) were made using p-methane hydroperoxide (MHP) as the catalyst. C-4 contained no water, while 1.51% of water was introduced into C-5.

|  | C-4 | C-5 |
|---|---|---|
| BisGMA | 6.34 | 6.03 |
| GDM-P | 15.82 | 15.08 |
| HEMA | 6.34 | 6.03 |
| ETMPTA | 3.17 | 3.02 |
| BHT | 0.05 | 0.05 |
| Water | — | 1.51 |
| MHP (55% active ingredient) | 1.78 | 1.78 |
| TS-530 | 2.00 | 2.00 |
| ST-OX-50 | 3.22 | 3.22 |
| Barium Glass | 61.28 | 61.28 |

The base B-3 of Example 2 was used to test the set times of catalyst pastes C-4 and C-5. The initial set time of freshly prepared pastes and set times after aging for various times are listed in following table. Similar to Example 2, the base was aged at room temperature, and the catalyst pastes were aged at 37° C.

| Set Time | C-4 | C-5 |
|---|---|---|
| Initial | 3'36" | 4'05" |
| 1 week | 3'49" | 4'18" |
| 2 weeks | 4'53" | 3'42" |
| 3 weeks | 6'40" | 4'36" |
| 4 weeks | 6'52" | 5'10" |
| 5 weeks | — | — |
| 6 weeks | 7'12" | 6'30" |

Again, shelf-stable adhesive cement systems were obtained utilizing self-cure initiator system comprising PTU and MHP (a hydroperoxide). Incorporation of water made the catalyst paste (C-5) slightly more stable.

Example 4

Two more catalyst pastes (C-6 and C-7) were made using 1,1,3,3-tetramethylbutyl hydroperoxide (TMBHP) and t-amyl hydroperoxide (TAHP) respectively.

|  | C-6 | C-7 |
|---|---|---|
| BisGMA | 6.23 | 6.23 |
| GDM-P | 19.67 | 19.67 |
| HEMA | 4.59 | 4.59 |
| ETMPTA | 2.30 | 2.30 |
| BHT | 0.05 | 0.05 |
| TMBHP/TAHP | 0.66 (TMBHP) | 0.66 (TAHP) |
| TS-530 | 2.00 | 2.00 |
| ST-OX-50 | 3.22 | 3.22 |
| Barium Glass | 61.28 | 61.28 |

A base paste (B-4) using PTU was made to test above two catalyst pastes.

|  | B-4 |
|---|---|
| BisGMA | 8.71 |
| UDMA | 7.26 |
| PEG400DMA | 4.36 |
| ETMPTA | 2.90 |
| HEMA | 5.81 |
| CQ | 0.09 |
| MEHQ | 0.015 |
| DMAPE | 0.13 |
| PTU | 0.72 |
| TS-530 | 3.00 |
| ST-OX-50 | 4.69 |
| Sr/Zn FAS Glass | 62.31 |

The initial set time as well as the set time after aging was listed in the following table. The catalyst pastes was stored at 37° C. and the base paste was stored at room temperature.

| Set Time | C-6 (TMBHP) | C-7 (TAHP) |
|---|---|---|
| Initial | 3'10" | 4'20" |
| 1 week | 4'40" | 5'26" |
| 2 weeks | 4'52" | 5'40" |
| 3 weeks | 5'00" | 6'55" |
| 4 weeks | 5'20" | — |
| 5 weeks | 5'16" | 6'40" |
| 6 weeks | 5'35" | 7'00" |

Again, shelf-stable adhesive cement systems were obtained utilizing self-cure initiator system comprising PTU as the activator and a hydroperoxide (TMBHP or TAHP) as catalyst.

Example 5

A base paste B-5 using PTU and a catalyst paste C-8 using pinane hydroperoxide (PHP) catalyst and two acidic monomers (GDM-P and PAMA) were made.

|  | B-5 |
| --- | --- |
| BisGMA | 8.40 |
| UDMA | 8.40 |
| HEMA | 11.21 |
| CQ | 0.08 |
| MEHQ | 0.015 |
| PTU | 0.39 |
| TS-530 | 3.00 |
| ST-OX-50 | 4.80 |
| Sr/Zn FAS Glass | 63.70 |

|  | C-8 |
| --- | --- |
| GDM-P | 19.67 |
| HEMA | 6.55 |
| PA-HEMA | 6.55 |
| BHT | 0.05 |
| CHP | 0.59 |
| PHP (55% active ingredient) | 0.59 |
| TS-530 | 2.00 |
| ST-OX-50 | 3.20 |
| Barium Glass | 60.80 |

When mixed at 1:1 ratio (weight), the above base and catalyst pastes had a set time of 4'38". Bonding strength tests to a dentine substrate were conducted using the above base and catalyst pastes (self-adhering cement). The dentine surface was polished with 600 grit SiC paper. The mixed base/catalyst pastes were directly applied to the dentine surface and bond strength was determined using an Instron Universal Tester (Model 4467) in shear mode using a crosshead speed of 0.05 inch per minute, after 24 hour conditioning in a high humidity chamber (85%-90% relative humidity at 37° C.). The curing was self-cure only (no light-curing). The mixed self-adhering cement paste had a dentine bond strength of 5.83 MPa (average of 7 specimens).

Example 6 base paste B-6 using PTU and a catalyst paste C-9 using 1,1,3,3-tetramethylbutyl hydroperoxide (TMBHP)/cumene hydroperoxide (CHP) catalysts and acidic monomers GDM-P were made.

|  | B-6 |
| --- | --- |
| UDMA | 22.00 |
| SR-454 | 5.50 |
| CQ | 0.17 |
| MEHQ | 0.010 |
| EDMAB | 0.28 |
| PTU | 0.54 |
| TS-530 | 3.00 |

-continued

|  | B-6 |
| --- | --- |
| ST-OX-50 | 4.80 |
| Sr/Zn FAS Glass | 63.70 |

|  | C-9 |
| --- | --- |
| BisGMA | 4.86 |
| GDM-P | 14.24 |
| HEMA | 5.82 |
| GDM | 4.21 |
| SR-454 | 3.24 |
| BHT | 0.05 |
| TMBHP | 0.54 |
| CHP | 0.54 |
| TS530 | 2.00 |
| ST-OX-50 | 3.23 |
| Barium Glass | 61.28 |

When mixed at a 1:4 (base:catalyst) ratio (weight), the above base and catalyst pastes had a set time of 5'48". Bonding strength tests to dentine substrate were conducted using the above base and catalyst pastes (self-adhering cement) using 1:4 (base:catalyst) ratio (by weight). The curing was self-cure only (no light-curing). The mixed self-adhering cement paste had a dentine bond strength of 9.28 MPa (average of 6 specimens).

The above examples demonstrate the usefulness of the self-cure initiator system comprising disclosed substituted thioureas as the activator and a hydroperoxide as the catalyst in formulating shelf-stable two-part acidic adhesive dental cement compositions. The substituted thiourea/hydroperoxide self-cure initiator system offers improvements over currently used self-cure initiator systems.

The inventive dental compositions can be used as a dental restorative composition, an endodontic composition, and an orthodontic composition. Useful restorative composition of current invention could be a dental filling material, a cement, a liner, a base, a pit/fissure sealant, a primer, or an adhesive composition. Useful endodontic composition could be an endodontic sealing and/or filling composition for the sealing and filling a root canal; also a endodontic primer, adhesive or cement for post cementation. Useful orthodontic composition could be an orthodontic adhesive or cement composition for adhering an orthodontic appliance to tooth surfaces.

Other variations or embodiments of the invention will also be apparent to one of ordinary skill in the art from the above descriptions and examples. Thus, the forgoing embodiments are not to be construed as limiting the scope of this invention.

What is claimed is:

1. A method for providing a two-part paste/paste dental composition to a tooth surface comprising the steps of:
   (I) etching a tooth surface with an etchant and/or priming the tooth surface with a primer/adhesive,
   (II) mixing two pastes of a two-part paste/paste composition to form a mixed composition immediately prior to application to the tooth surface,
   (III) applying the mixed composition to the tooth surface, and
   (IV) hardening the mixed composition,
wherein the two-part paste/paste composition comprises a first paste comprising (a) at least one polymerizable monomer with a polymerizable group selected from the group consisting of an acrylate, a methacrylate, and a vinyl group;
(b) a substituted thiourea selected from the group consisting of 1-(2-pyridyl)-2-thiourea and 1-(2-tetrahydrofurfuryl)-2-thiourea; and
(c) a finely divided filler having a mean particle size of less than 50 microns; and a second paste comprising
(d) at least one acidic compound containing at least one acidic moiety selected from the group consisting of

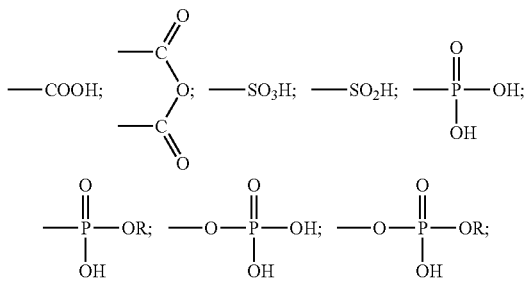

where R is an alkyl or aryl group;
(e) at least one polymerizable monomer without any acidic group with a polymerizable group selected from the group consisting of an acrylate, a methacrylate, and a vinyl group;
(f) a hydroperoxide compound with at least one hydroperoxide group attached to a tertiary carbon; and
(g) a finely divided filler having a mean particle size less than 50 microns.

2. The method of claim 1 wherein the two part composition further comprises at least one component selected from the group consisting of a photo-initiator, a stabilizer, a solvent, and combinations thereof.

3. The method of claim 1 wherein the filler is selected from the group consisting of inorganic metal, salt, oxide, nitride, silicate glass, aluminosilicate glass, aluminoborosilicate glass, fluoroaluminosilicate glass, quartz, colloidal silica, precipitated silica, zirconia-silica, polymeric filler, polymerized composite filler with inorganic particles, and combinations thereof.

4. The method of claim 1 wherein the acidic compound is a polymerizable monomer/polymer with at least one ethylenically unsaturated group selected from the group consisting of an acrylate, a methacrylate, and a vinyl group.

5. The method of claim 4 wherein the acidic polymerizable monomer is selected from the group consisting of hydroxyethylmethacrylate phosphate (HEMA-P), glyceryldimethacrylate phosphate (GDM-P), bis(hydroxyethylmethacrylate) phosphate (Bis(HEMA)-P), methacryloyloxydecyl phosphate (MDP), phenyl methacryloxyethyl phosphate (phenyl-P), and dipentaerythritol pentaacrylate phosphate (PENTA-P).

6. The method of claim 1 wherein the hydroperoxide compound is selected from the group consisting of t-butyl hydroperoxide, t-amyl hydroperoxide, p-diisopropylbenzene hydroperoxide, cumene hydroperoxide, pinane hydroperoxide, p-menthane hydroperoxide, 1,1,3,3-tetramethylbutyl hydroperoxide, and combinations thereof.

7. The method of claim 1 wherein each part of the two part composition is packaged in a syringe.

8. The method of claim 1 wherein each part of the two part composition is packaged in a syringe in a dual syringe assembly.

9. The method of claim 8 wherein each syringe in the dual syringe assembly has an opening and a static mixer is attached to the openings and provides a homogeneous mixture upon dispensing the mixed composition from an exit opening of the mixer.

10. The method of claim 1 wherein the composition is applied to a tooth surface as at least one of a restorative composition, an orthodontic composition, or an endodontic composition.

11. The method of claim 1 wherein the composition is applied to a tooth surface as at least one of a filling material, a cement, a liner/base, a pit/fissure sealant, or an adhesive composition.

* * * * *

UNITED STATES PATENT AND TRADEMARK OFFICE
CERTIFICATE OF CORRECTION

PATENT NO. : 7,351,753 B2
APPLICATION NO. : 11/612039
DATED : April 1, 2008
INVENTOR(S) : Xuejun Qian It is certified that error appears in the above-identified patent and that said Letters Patent is hereby corrected as shown below:

Col. 1, line 26, "cement is mixed" should read --cement are mixed--.

Col. 2, line 27, "where the polymerizable polymerizable group" should read --where the polymerizable group--.

Col. 5, line 33, "consisting an acrylate," should read --consisting of an acrylate,--.

Col. 5, line 45, "consisting of following" should read --consisting of the following--.

Col. 7, line 58, "the two-parts are mixed" should read --the two parts are mixed--.

Col. 8, line 24, "as Sr, Y., Zr, Ba, La," should read --as Sr, Y, Zr, Ba, La,--.

Col. 10, lines 59-60 should be one continuous paragraph.

Col. 11, line 5, "that has an mean particle" should read --that has a mean particle--.

Col. 11, line 26, "that has an mean" should read --that has a mean--.

Col. 11, line 36, "diisocynate" should read --diisocyanate--.

Col. 11, line 50, "and the then the fillers" should read --and then the fillers--.

Col. 12, line 20, "formulations that contains" should read --formulations that contain--.

Col. 14, line 54, "The catalyst pastes was stored" should read --The catalyst pastes were stored--.

Col. 15, line 53, "base paste B-6" should read --A base paste B-6--.

Col. 16, line 19, "TS530" should read --TS-530--.

UNITED STATES PATENT AND TRADEMARK OFFICE
CERTIFICATE OF CORRECTION

PATENT NO.        : 7,351,753 B2
APPLICATION NO. : 11/612039
DATED             : April 1, 2008
INVENTOR(S)       : Xuejun Qian It is certified that error appears in the above-identified patent and that said Letters Patent is hereby corrected as shown below:

Col. 16, line 52, "the forgoing" should read --the foregoing--.

Signed and Sealed this

Twelfth Day of May, 2009

JOHN DOLL
*Acting Director of the United States Patent and Trademark Office*